United States Patent [19]
Sampath

[11] Patent Number: 5,649,281
[45] Date of Patent: Jul. 15, 1997

[54] ALKYLATION WITH SEPARATE ALKYLATION OF ISOBUTANE WITH PENTENES

[75] Inventor: Vijay R. Sampath, Brea, Calif.

[73] Assignee: Atlantic Richfield Company, Los Angeles, Calif.

[21] Appl. No.: 440,275

[22] Filed: Jul. 17, 1995

Related U.S. Application Data

[62] Division of Ser. No. 169,850, Dec. 17, 1993, abandoned.
[51] Int. Cl.⁶ .................. B01J 10/00; B01J 19/00
[52] U.S. Cl. .......... 422/189; 585/301; 585/300; 585/302; 585/331; 585/716; 585/717
[58] Field of Search .................. 585/301, 300, 585/716, 717, 331, 302; 422/189

[56] References Cited

U.S. PATENT DOCUMENTS 4,304,947  12/1981  Hutson, Jr. .................. 585/301

Primary Examiner—Glenn A. Caldarola
Assistant Examiner—Nadine Preisch
Attorney, Agent, or Firm—Tom F. Pruitt

[57] ABSTRACT

A process is provided to react a feedstock comprising isobutane with pentenes in the presence of sulfuric acid catalyst to produce a high octane alkylate as well as a higher octane isopentane gasoline blending component. A method to reduce sulfuric acid consumption during alkylation is provided wherein a diolefinic contaminant of a pentene system feed is selectively hydrogenated before alkylation. An alkylation method is provided wherein the alkylation feed is separated into a fraction comprising substantially $C_4$ and lower olefins and a fraction comprising substantially $C_5$ olefins and the stream comprising $C_5$ olefins is alkylated in a different reactor than the fraction comprising substantially $C_4$ and lower olefins.

8 Claims, 2 Drawing Sheets

ALKYLATION WITH SEPARATE ALKYLATION OF ISOBUTANE WITH PENTENES

This is a division of application Ser. No. 08/169,850 filed Dec. 17, 1993 now abandoned.

BACKGROUND OF THE INVENTION

1. Field of the Invention

In one aspect, this invention relates to alkylation of isobutane with pentenes. In another aspect, this invention relates to a process to react a feedstock comprising isobutane with pentenes in the presence of sulfuric acid catalyst to produce a high octane alkylate as well as a higher octane isopentane gasoline blending component. In still another aspect, this invention relates to a method to reduce sulfuric acid consumption during alkylation.

2. Background

Federal and state clean air regulations related to motor vehicle fuels have imposed a requirement for reduced olefinic content of gasoline. Olefins in gasolines are considered by many to be major ozone precursors. Also, certain regulations severely limit the amount of pentenes (or amylenes) that can be directly blended into gasoline because of their relatively high Bromine number and contribution to higher Reid Vapor Pressure.

With these new clean air regulations, refiners are directing attention to removing pentenes from the gasoline pool.

For over fifty years, mixed olefinic feedstreams have been reacted with an isobutane feed to produce alkylate. These mixed olefinic feedstreams comprise propylene, butenes, and pentenes. Although $C_4$ olefins (mixed butenes) have been the principal component of mixed olefinic feedstocks fed to alkylation units, a typical alkylation olefin feed stream comprises both $C_3$ olefins and $C_5$ olefins (mixed pentenes).

The mixed butenes include isobutylene, 1-butene, trans-2-butene, and cis-2-butene. The $C_4$ and lower portion of the feed stream also contains diolefinic contaminants such as 1,3-butadiene. The mixed pentenes typically include 1-pentene, trans-2-pentene, cis-2-pentene, 2-methylbutene-1, 2-methylbutene-2, 3-methylbutene-1 and cyclopentene. The $C_5$ and higher portion of the feed stream also contains diolefinic contaminants such as 2-methyl-1,3-butadiene, 3-methyl-1,2-butadiene, 1,3-pentadiene and cyclopentadiene.

It has been reported that pentenes, when alkylated, produce a complex alkylate with many products, due in part to the greater number of olefins possible in the pentene system as compared to the propylene or butene system. For the pentene system, it is also reported that the primary alkylation products are more inclined to undergo rearrangement and cleavage than those from lighter olefins and that hydrogen transfer occurs more readily than with lower olefins. It is also known in the art that $C_5$ feeds typically contain more diolefins than $C_4$ olefin feeds, and that the $C_5$ feeds should be selectively hydrogenated to reduce acid consumption during alkylation that is otherwise caused by competing reactions which result from the presence of the diolefins.

Since pentenes have long been a portion of alkylation unit feed, increasing the pentene portion of such feed is one approach to removing pentenes from the gasoline pool.

Certain procedures for alkylating streams containing $C_5$ olefins and the quality of the alkylate made from such streams are discussed in the prior art as, for example, in the article entitled "$H_2SO_4$ Alkylation Shows Promise for Upgrading Gasoline Pentenes" published in the Feb. 17, 1992 edition of the Oil & Gas Journal at pages 72 to 74.

The prior art, as confirmed by such article, has recognized no benefits or penalties associated with combined or separate alkylation of the $C_3$, $C_4$, and $C_5$ feed materials. The prior art thus teaches that there is no specific advantage to processing $C_5$ olefins separately and teaches that refiners should co-process $C_5$ olefins along with $C_4$ and $C_3$ olefins.

SUMMARY OF THE INVENTION

I have invented a process to separately alkylate $C_5$ olefins that results in a significant economic advantage as compared to co-processing $C_5$ olefins along with $C_4$ and $C_3$ olefins. I have found that separate alkylation of a feedstock comprising isobutane with pentenes can produce, in an economically attractive manner, a high octane alkylate as well as a higher octane isopentane gasoline blend component. I have also found that sulfuric acid consumption during alkylation can be reduced by separating alkylation feed into a fraction comprising substantially $C_4$ and lower components and a fraction comprising substantially $C_5$ and higher components and optimizing the conditions of the $C_5$ alkylation for minimum acid consumption. I have further found that alkylation equipment capital costs may be reduced and sulfuric acid consumption, during alkylation can be reduced by separating alkylation feed into a fraction comprising substantially $C_4$ and lower components and a fraction comprising substantially $C_5$ and higher components and then selectively hydrogenating the diolefinic contaminants found in the $C_5$ and higher fraction before separately alkylating such fraction.

In accordance with 6he embodiment of this invention, an alkylation process for alkylating isobutane with components of a feed comprising mixed butenes and mixed pentenes, and further comprising one or more of propane, normal butane, a $C_4$ diolefin or a $C_5$ diolefin, comprises (a) separating the feed into a fraction comprising substantially mixed butenes and compounds which are lower boiling than said mixed butenes and a fraction comprising substantially mixed pentenes; (b) alkylating the isobutane with the fraction comprising substantially the mixed butenes and the lower boiling compounds; and, (c) separately alkylating the isobutane with the fraction comprising substantially the mixed pentenes. In one variation of this embodiment, the fraction comprising substantially mixed pentenes further comprises a $C_5$ diolefin and before the fraction comprising substantially mixed pentenes is alkylated, the $C_5$ diolefin is selectively hydrogenated in the presence of hydrogenating catalyst with added hydrogen at elevated temperature and pressure sufficient to saturate at least one unsaturated bond of the $C_5$ diolefin. In another variation of this embodiment, the $C_5$ diolefin is from the group consisting of 2-methyl-1,3-butadiene, 3-methyl-1,2-butadiene, 1,3-pentadiene and cyclopentadiene.

In another embodiment of this invention, a process to produce a high octane alkylate as well as a higher octane isopentane gasoline blend component comprises (a) reacting isobutane in a first reactor with a feed comprising substantially butenes and butane, propane and other lower boiling compounds in the presence of excess isobutane and sulfuric acid catalyst to form a first product stream comprising alkylate, excess isobutane, normal butane, propane and other compounds which are lower boiling than butenes; (b) reacting isobutane in a second reactor with a feed comprising substantially pentenes in the presence of excess isobutane and sulfuric acid catalyst to form a second product stream comprising high octane alkylate, excess isobutane, normal butane and propane and other lower boiling compounds and a higher octane isopentane gasoline blending component; (c) separating propane from at least a portion of the first and second product streams in a common depropanizer; (d) separating normal butane from at least a portion of the first and second product streams in a common debutanizer; (e) separating and recovering the high octane alkylate from the second product stream; and, (f) separating and recovering the higher octane isopentane gasoline blending component from the second product stream.

In another embodiment of this invention, a method to reduce sulfuric acid consumption during alkylation, in presence of sulfuric acid, of isobutane with an alkylation feed comprising $C_4$ and lower olefins and comprising $C_5$ olefins and a $C_5$ diolefinic contaminant, comprises (a) separating the alkylation feed into a fraction comprising substantially $C_4$ and lower olefins and a fraction comprising substantially $C_5$ olefins and the $C_5$ diolefinic contaminant; (b) selectively hydrogenating the $C_5$ diolefinic contaminant of the fraction comprising substantially $C_5$ olefins and $C_5$ diolefinic contaminant to form a stream comprising $C_5$ olefins and reduced content of diolefinic contaminant; (c) alkylating the stream comprising $C_5$ olefins and reduced content of diolefinic contaminant; and, (d) separately alkylating the fraction comprising substantially $C_4$ and lower olefins. In one variation of this embodiment of this invention, the $C_5$ diolefinic contaminant is from the group consisting of 2-methyl-1,3-butadiene, 3-methyl-1,2-butadiene, 1,3-pentadiene and cyclopentadiene. In another variation of this embodiment, the selective hydrogenation is carried at in the presence of hydrogenating catalyst, as are well known it art, with added hydrogen at elevated temperature and pressure sufficient to saturate at least one unsaturated bond of the diolefinic contaminant. In still another variation of this embodiment, the alkylation feed comprises paraffins selected from the group consisting of $C_3$, $C_4$, and $C_5$ paraffins.

In a still further embodiment of this invention, a combination of alkylation apparatus comprises (a) a first reactor for reacting isobutane with a feed comprising substantially butenes and lower boiling compounds in the presence of excess isobutane and sulfuric acid catalyst to form spent acid and a first product stream comprising alkylate, excess isobutane, normal butane and propane; (b) a second reactor for reacting isobutane with a feed comprising substantially pentenes in the presence of excess isobutane and sulfuric acid catalyst to form a second product stream comprising alkylate, excess isobutane, normal butane and propane a common depropanizer to separate propane from at least a portion of the first and second product streams. In another variation, the apparatus further comprises a common debutanizer to separate normal butane from at least a portion of the first and second product streams. The term "common" as used when referring to a fractionating unit or tower such as a depropanizer or debutanizer or the like in the Specification and Claims is meant a shared tower to which is fed two or more process streams from separate reaction trains. In a variation of this embodiment, the apparatus comprises a conduit to direct the first spent acid to the second reactor.

DESCRIPTION OF PREFERRED EMBODIMENTS

Figure 1:
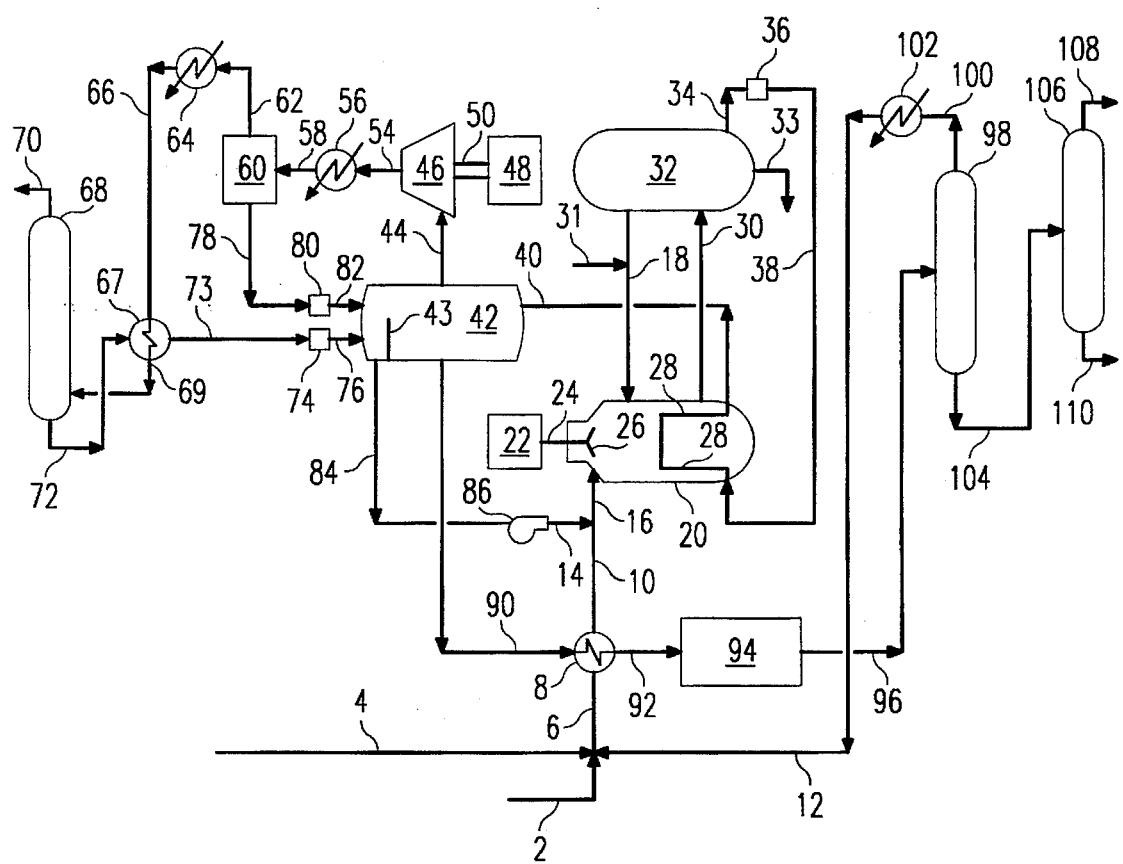
FIG. 1 is a schematic diagram of prior art combined alkylation of $C_3$, $C_4$, and $C_5$ feed materials.

In FIG. 1, a prior art process for combined alkylation of $C_3$, $C_4$, and $C_5$ feed materials using $H_2SO_4$ as the catalyst in an effluent refrigeration process. A make-up isobutane feed 2 is combined with first isobutane rich recycle feed stream 12 and a feed 4 comprising $C_3$, $C_4$, and $C_5$ materials in conduit 6. The combined feed 6 is preferably cooled by cooler 8 to form cooled combined stream 10. The coolant 90 for cooler 8 may be another process stream having a temperature lower than that of stream 6. To the cooled combined isobutane and $C_3$, $C_4$, and $C_5$ feed stream 10 is added a second isobutane rich recycle feed stream 14 to form reactor 20 hydrocarbonaeous feed 16. The reactor 20 co-processes the $C_5$ olefins along with $C_4$ and $C_3$ olefins in the feed 16. A sulfuric acid feed 18 is also fed to the reactor 20. Drive motor 22 drives shaft 24 which moves mixing device 26 to form a two phase hydrocarbon-acid emulsion (not shown) in the reactor 20, and the hydrocarbon-acid emulsion is circulated through the reactor 20 and in contact with a heat exchanger tube bundle shown generally as 28 to remove the exothermic heat of alkylation. A continuous flow of the reactor 20 effluent 30 is withdrawn and directed to an acid decanter 32. The decanter 32 conditions are adjusted such that the residence time of the decanter 32 contents allow essentially complete separation of sulfuric acid from the hydrocarbon, and the hydrocarbon phase 34 substantially free of acid is withdrawn from decanter 32. An emulsion (not shown) made up of hydrocarbon and acid is recycled back to the reactor 20 as acid feed 18. To the acid feed 18 is added fresh acid 31 make-up. In addition, a draw of spent acid 33 is taken from the decanter 32 to maintain the strength (e.g. relative concentration of sulfuric acid) of stream 18 at the desired level. For example, it is known in the art that the octane number of alkylate made from $C_4$ and lighter olefins varies significantly with the average strength of the sulfuric acid employed in reactor 20, and it is known, that generally, the octane of alkylate produced increases is average sulfuric acid strength increases. The hydrocarbon phase 34 is flashed through a pressure reducing device 36 where the isobutane and more volatile hydrocarbons are vaporized to formed cold hydrocarbonaeous coolant stream 38 which is two phases, a gas phase and a liquid. This coolant stream 38 is partially vaporized through the reactor 20 tube bundle 28 as coolant providing "effluent refrigeration" and is passed via conduit 40 from the reactor 20 to a flash drum 42. The flash drum 42 separates the mixed feeds 76, 82, and 40 into vapor and liquid. Those skilled in the art understand that flash drum 42 is divided into two separate zones (not shown) or contains an internal decanting baffle 43 or other separation means to facilitate separation of isobutane rich stream 84 from alkylate rich stream 90. The vapor 44 is primarily isobutane but contains some propane and $C_5$ and higher hydrocarbons. This vapor 44 is compressed by compressor 46 which is driven by motor 48 and shaft 50 and is then passed via conduit 54 to cooler 56 where a partially condensed stream 58 is formed. The partially condensed stream 58 is passed to separator 60 where an overhead gaseous stream 62 is cooled via cooler 64 and passed via conduit 66 to depropanizer 68 feed bottoms heat exchanger 67. The depropanizer 68 feed 66 is heated by heat exchanger 67 by exchange of heat from hot isobutane bottoms product 72 from the depropanizer 68 to form heated depropanizer feed 69 and cooled bottoms product 73 which is predominately isobutane and which is flashed via pressure reducing device 74 before being passed via conduit 76 to flash drum 42. Via fractionation of stream 66 in depropanizer 68, a propane rich stream 70 is removed from overhead from depropanizer 68 and a bottom product 72 is produced. A liquid stream 78 is taken from the separator 60 and flashed via pressure reducing device 80 and thus cooled before being passed via conduit 82 to flash drum 42. A cold liquid stream 84, comprising primarily isobutane, is withdrawn from the flash drum 42 and pumped via pump 86 to form the refrigerant recycle stream 14 which serves both as a reactant and a coolant. The flash drum 42 cool effluent 90 can serve as coolant for cooler 8, and as shown, is passed via conduit 92 to effluent treating unit 94. The alkylate rich flash drum effluent 90 and 92 comprises primarily alkylate and isobutane along with some normal butane and certain contaminants such as sulfates, residual acid and water. In the effluent treating unit 94, which can consist of a series of vessels, the effluent is treated with fresh acid to react with the sulfates and with caustic solution to remove residual acid and other reactive materials. The treated effluent 96 is passed to a deisobutanizer tower where a column overhead product 100 which comprises primarily isobutane is cooled via cooler 102 to form the cool first isobutane rich recycle feed stream 12. The bottoms 104 from the deisobutanizer 98 comprises alkylate and normal butane. Stream 104 is fed to debutanizer tower 106 were a $C_4$ and lighter product 108 is removed overhead and a $C_5$ and higher and alkylate product 110 is removed from the bottoms.

Figure 2:
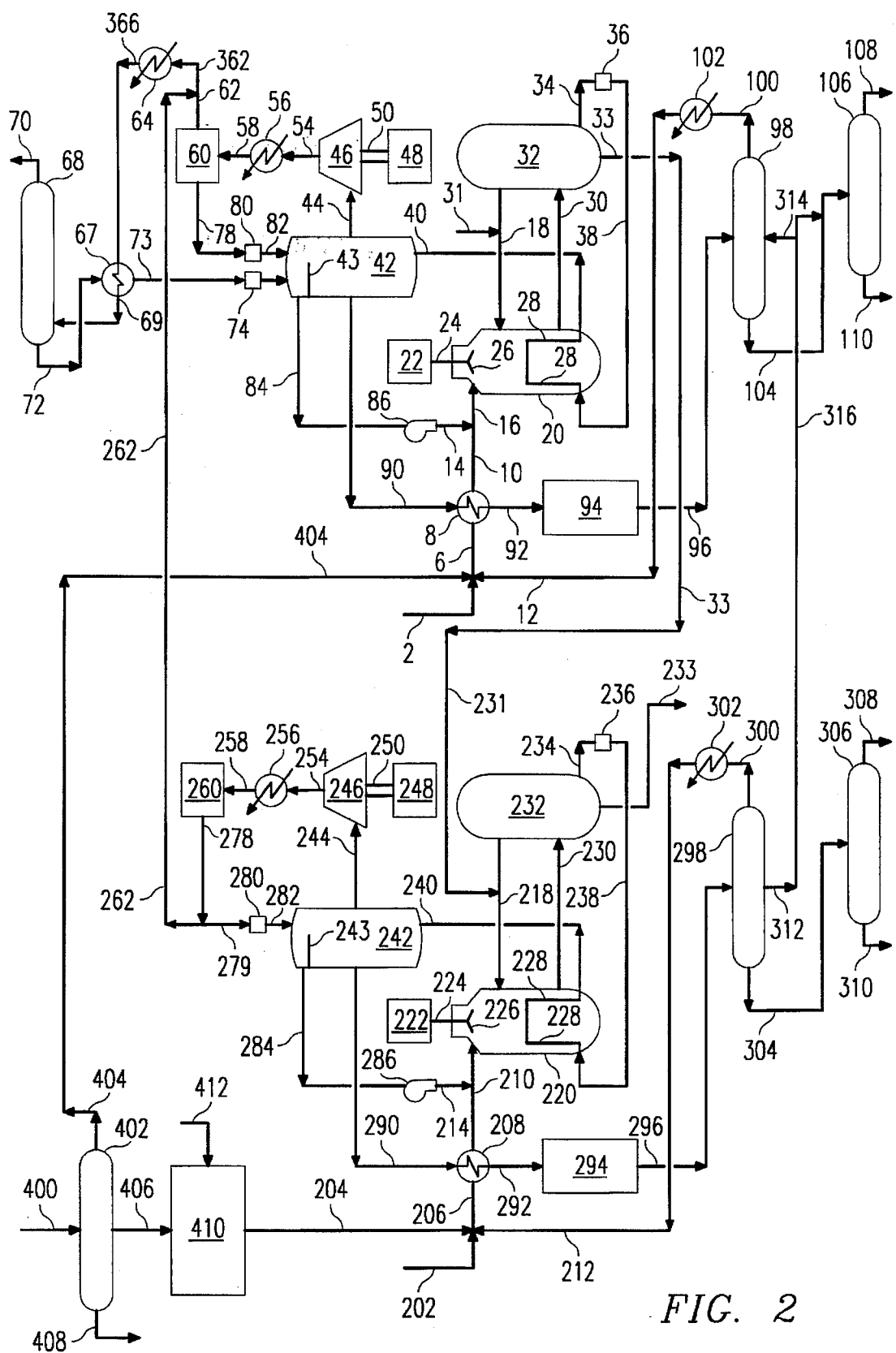
FIG. 2 is a schematic representation of one variation of one embodiment of an alkylation process of this invention.

In FIG. 2, one variation of one embodiment of an alkylation process of this invention is shown. Certain numbers used in FIG. 1 are used in FIG. 2, and as used, have the same meaning as assigned in the foregoing description of FIG. 1. Feed 400 comprising $C_3$, $C_4$, and $C_5$ olefins and heavier materials is fed to a fractionating system 402, comprising one or more fractionators, wherein the feed 400 is cut into three streams: to wit, a predominately $C_3$ and $C_4$ stream 404, a predominately $C_6$ and heavier stream 408, and a predominately $C_5$ stream 406. The $C_6$ and heavier materials 408 can be removed and used as gasoline blendstock or directed to further processing to eliminate undesired heavy components.

The predominately $C_3$ and $C_4$ stream 404 is preferably used as feed to a conventional alkylation unit which is configured as was described in FIG. 1 (and stream 404 is substituted for feed numeral 4 of FIG. 1) and is alkylated in a manner similar to that described in FIG. 1, except considering the $C_5$ range materials are not present in feed 404.

One advantage obtained from this embodiment is reduced acid consumption in reactor 20 because the $C_5$ diolefins which increase acid consumption in conventional alkylation reactor 20 are removed from the reactor 20 feed 16. Another advantage is that since pentenes 406, when alkylated, produce a complex alkylate with many products, due in part to the greater number of olefins possible in the pentene system as compared to the propylene or butene system, a more consistent and higher quality alkylate 110 is produced from a feed 404 without $C_5$ materials 406.

Again referring to FIG. 2, $C_5$ range materials 406 are preferably fed to a processing unit 410, such as a selective hydrogenation unit with added hydrogen 412, to pretreat feed stream 406 and saturate diolefins to form an alkylation feed 204 low in diolefinic material.

A make-up isobutane feed 202 is combined with an isobutane rich recycle feed 212 and with feed 204 comprising $C_5$ olefinic range materials in conduit 206. The combined feed 206 is preferably cooled by cooler 208 to form cooled combined stream 210. The coolant 290 for cooler 208 may be another process stream having a temperature lower than that of stream 206. To the cooled combined isobutane and $C_5$ range feed stream 210 is added another isobutane rich recycle feed stream 214 to form reactor 220 hydrocarbonaceous feed 216. In a configuration preferably similar to that of reactor 20, reactor 220 has a sulfuric acid feed 218, drive motor 222, drive shaft 224 and mixing device 226 which form a two phase hydrocarbon-acid emulsion (not shown) with acid feed 218 and reactor 220 hydrocarbon feed 216, and reactor 220 also has a cooling heat exchanger tube bundle shown generally as 228. A continuous flow of the reactor 220 effluent 230 is withdrawn and directed to an acid decanter 232 where reactor 220 effluent 230 is separated into a separate liquid phase comprising acid and some hydrocarbon which is recycled as acid feed 218 and a substantially liquid hydrocarbon phase 234 which is withdrawn from the decanter 232. In addition, a draw of spent acid 233 is taken from the decanter 232 to maintain the strength (e.g. relative concentration of sulfuric acid) of stream 218 at the desired level. In one preferred variation of this embodiment, a draw of spent acid 33 from decanter 32 is passed via conduit 231 as make-up acid feed for reactor 220. The hydrocarbon phase 234 is flashed through a pressure reducing device 236 where the isobutane and more volatile hydrocarbons are vaporized to form cold hydrocarbonaeous coolant stream 238 which is two phases, a gas phase and a liquid. This coolant stream 238 is partially vaporized through the reactor 220 tube bundle 228 as coolant and is passed via conduit 240 from the reactor 220 to a flash drum 242. The flash drum 242 separates the mixed feeds 282, and 240 into vapor and liquid. Flash drum 242 is divided into two separate zones (not shown) or contains an internal baffle 243 or other means to facilitate separation of isobutane rich stream 284 from alkylate rich stream 290. The flashed vapor stream 244 is primarily isobutane but contains some propane and $C_5$ and higher hydrocarbons. This stream 244 is compressed by compressor 246 which is driven by motor 248 and shaft 250 and is then passed via conduit 254 to cooler 256 where stream 258, which is preferably totally condensed, is formed. The condensed stream 258 is passed to accumulator 260. A slip stream 278 and 262 is withdrawn via conduit 362 through cooler 64 and via conduits 366 and 69 to depropanizer 68. A liquid stream 278 is taken via conduit 279 from the accumulator 260 and flashed via pressure reducing device 280 and thus cooled before being passed via conduit 282 to flash drum 242. A cold liquid stream 284, comprising primarily isobutane, is withdrawn from the flash drum 242 and pumped by pump 286 to form refrigerant recycle stream 214 which serves both as a reactant and a coolant. The flash drum 242 cool effluent 290 can serve as coolant for cooler 208, and as shown, is passed via conduit 292 to effluent treating unit 294. The flash drum effluent 290 and 292 comprises primarily alkylate, isopentane, and isobutane along with some normal butane and certain contaminants such as sulfates, residual acid and water. The effluent is treated in effluent treating unit 294 for removal of sulfates, residual acid and other reactive materials. The treated effluent 296 is passed to a deisobutanizer tower 298 where column 298 overhead product 300 which comprises primarily isobutane is cooled via cooler 302 to form the cool isobutane rich recycle feed stream 212.

From the deisobutanizer 298, a cut comprising normal butane may be withdrawn via conduit 312 and directed either to deisobutanizer 98 or to debutanizer 106 for recovery.

The bottoms 304 from the deisobutanizer 298 comprises alkylate and isopentane and other desirable high octane gasoline blending components. Stream 304 is fed to depentanizer tower 306 where an alkylate product 310 is removed from the tower 306 bottoms and a desirable higher octane blending stream 308 comprising primarily isopentane is removed from the tower 306 overhead.

Another advantage from this embodiment shown in FIG. 2 is that $C_5$ reactor 220 alkylation system does not require the capital for a separate depropanizer 68 or separate debutanizer 106.

A key advantage with the embodiment shown in FIG. 2, not available with prior art alkylation as shown in FIG. 1, is that reaction and system conditions of $C_5$ reactor 220 alkylation system can be optimized for minimum acid 218 consumption. That is, prior art processes as shown in FIG. 1 are optimized to maximize octane of product 110 often at penalty of higher acid 18 consumption. Opposite thereto, in the pentene system feed 406 alkylation the ratio of isobutane feeds 202, 212, and 214 to $C_5$ olefin 204 feed can be adjusted and tailored for optimum $C_5$ group conversion. In addition, more effective reactor 220, decanter 232, flash drum 242, and compressor 246 process variable settings can be selected for optimum $C_5$ group conversion.

As discussed above, octane number of alkylate made from $C_4$ and lighter olefins varies significantly with the average strength of the sulfuric acid employed in the alkylation reactor, and generally, the alkylate's octane increases as average sulfuric acid strength increases. On the other hand, the octane of alkylate produced from $C_5$ olefin feed is not affected significantly by acid quality, except for major losses of acid strength. The embodiment of this invention as shown in FIG. 2 thus provides an advantageous way to integrate two alkylation units (e.g unit employing reactor 20 with $C_4$ and lighter olefin feed and unit employing reactor 220 $C_5$ olefin feed). Preferably, sulfuric acid is directed in a series flow first to the unit employing reactor 20 followed by the unit employing reactor 220. More preferably, fresh acid 31 is fed to unit employing reactor 20 with $C_4$ and lighter olefin feed with spent acid 33 from the unit employing reactor 20 with $C_4$ and lighter olefin feed being routed via conduits 33 and 231 to the unit employing reactor 220 and $C_5$ olefin feed, with a final spent acid 233 being withdrawn from decanter 232, as shown in FIG. 2.

Variations in the foregoing invention may be made without departing from the spirit and scope thereof.

I claim:

1. A combination of alkylation apparatus comprising:

a. a first reactor for reacting isobutane with a first feed comprising substantially butenes and lower boiling compounds in the presence of excess isobutane and sulfuric acid catalyst to form a first reactor effluent comprising a first spent acid, a first alkylate, excess isobutane, normal butane and propane;

b. a first acid decanter in fluid communication with the first reactor through a first conduit which conveys the first reactor effluent to the first acid decanter, which decanter separates said first reactor effluent into a first hydrocarbon phase and a first acid recycle phase;

c. a first flash drum in fluid communication with the first acid decanter through a second conduit which conveys the first hydrocarbon phase to the first flash drum, which drum separates the first hydrocarbon phase into a first isobutane recycle stream, a first alkylate-containing stream, and a first mixed hydrocarbon slip stream comprised of propane and higher hydrocarbons;

d. a first deisobutanizer in fluid communication with the first flash drum through a third conduit which conveys the first alkylate-containing stream to the first deisobutanizer, which deisobutanizer separates the first alkylate-containing stream into a second isobutane recycle stream and a first alkylate-rich intermediate product;

e. a second reactor for reacting isobutane with a second feed comprising substantially pentenes in the presence of excess isobutane and sulfuric acid catalyst to form a second reactor effluent comprising a second spent acid, a second alkylate, excess isobutane, normal butane, and propane;

f. a second acid decanter in fluid communication with the second reactor through a fourth conduit which conveys the second reactor effluent to the second acid decanter, which decanter separates the second reactor effluent into a second hydrocarbon phase and a second acid recycle phase;

g. a second flash drum in fluid communication with the second acid decanter through a fifth conduit which conveys the second hydrocarbon phase to the second flash drum, which drum separates said second hydrocarbon phase into a third isobutane recycle stream, a second alkylate-containing stream, and a second mixed hydrocarbon slip stream comprised of propane and higher hydrocarbons;

h. a second deisobutanizer in fluid communication with the second flash drum through a sixth conduit which conveys the second alkylate-containing stream to the second deisobutanizer, which deisobutanizer separates the second alkylate-containing stream into a fourth isobutane recycle stream and a second alkylate-rich intermediate product, the second deisobutanizer also producing a n-butane rich slid stream;

i. a common depropanizer in fluid communication with (1) the first flash drum through a seventh conduit which conveys the first mixed hydrocarbon slip stream to the common depropanizer, and (2) the second flash drum through an eighth conduit which conveys the second mixed hydrocarbon slip stream from the second flash drum to the common depropanizer, the common depropanizer separating the first mixed hydrocarbon slip stream and the second mixed hydrocarbon slip stream into a propane-rich product and a fifth isobutane recycle stream;

j. a common debutanizer in fluid communication with (1) the first deisobutanizer through a ninth conduit which conveys the first alkylate-rich intermediate product to the common debutanizer, and (2) the second deisobutanizer through a tenth conduit which conveys the n-butane rich slip stream from the second deisobutanizer to the common debutanizer, the common debutanizer separating the first alkylate-rich intermediate product and the n-butane rich slip stream into a n-butane and lighter hydrocarbon product and a first alkylate product; and k. a depentanizer in fluid communication with the second deisobutanizer through an eleventh conduit which receives the second alkylate-rich intermediate product and separates said intermediate product into a higher octane blending product comprised of isopentane, and a second alkylate product.

2. An apparatus in accordance with claim 1 further comprising a twelfth conduit which directs at least a portion of said first acid recycle phase from the first acid decanter to said second reactor.

3. An apparatus in accordance with claim 1 wherein the tenth conduit is adapted to direct at least a portion of the n-butane rich slip stream from the second deisobutanizer to the first deisobutanizer.

4. A combination of alkylation apparatus comprising:

a. a first reactor for reacting isobutane with a first feed comprising substantially butenes and lower boiling compounds in the presence of excess isobutane and sulfuric acid catalyst to form a first reactor effluent comprising a first spent acid, a first alkylate, excess isobutane, normal butane and propane;

b. a first acid decanter in fluid communication with the first reactor through a first conduit which conveys the first reactor effluent to the first acid decanter, which decanter separates said first reactor effluent into a first hydrocarbon phase and a first acid recycle phase;

c. a first flash drum in fluid communication with the first acid decanter through a second conduit which conveys the first hydrocarbon phase to the first flash drum, which drum separates the first hydrocarbon phase into a first isobutane recycle stream, a first alkylate-containing stream, and a first mixed hydrocarbon slip stream comprised of propane and higher hydrocarbons;

d. a second reactor for reacting isobutane with a second feed comprising substantially pentenes in the presence of excess isobutane and sulfuric acid catalyst to form a second reactor effluent comprising a second spent acid, a second alkylate, excess isobutane, normal butane, and propane;

e. a second acid decanter in fluid communication with the second reactor through a third conduit which conveys the second reactor effluent to the second acid decanter, which decanter separates the second reactor effluent into a second hydrocarbon phase and a second acid recycle phase;

f. a second flash drum in fluid communication with the second acid decanter through a fourth conduit which conveys the second hydrocarbon phase to the second flash drum, which drum separates said second hydrocarbon phase into a second isobutane recycle stream, a second alkylate-containing stream, and a second mixed hydrocarbon slip stream comprised of propane and higher hydrocarbons; and g. a common depropanizer in fluid communication with (1) the first flash drum through a fifth conduit which conveys the first mixed hydrocarbon slip stream to the common depropanizer, and (2) the second flash drum through an sixth conduit which conveys the second mixed hydrocarbon slip stream from the second flash drum to the common depropanizer, the common depropanizer separating the first mixed hydrocarbon slip stream and the second mixed hydrocarbon slip stream into a propane-rich product and a third isobutane recycle stream.

5. An apparatus in accordance with claim 4 further comprising a seventh conduit which directs at least a portion of said first acid recycle phase from the first acid decanter to said second reactor.

6. A combination of alkylation apparatus comprising:

a. a first reactor for reacting isobutane with a first feed comprising substantially butenes and lower boiling compounds in the presence of excess isobutane and sulfuric acid catalyst to form a first reactor effluent comprising a first spent acid, a first alkylate, excess isobutane, normal butane and propane;

b. a first acid decanter in fluid communication with the first reactor through a first conduit which conveys the first reactor effluent to the first acid decanter, which decanter separates said first reactor effluent into a first hydrocarbon phase and a first acid recycle phase;

c. a first deisobutanizer in fluid communication with the first acid decanter through a second conduit which conveys the first hydrocarbon phase to the first deisobutanizer, which deisobutanizer separates the first hydrocarbon phase into a first isobutane recycle stream and a first alkylate-rich intermediate product;

d. a second reactor for reacting isobutane with a second feed comprising substantially pentenes in the presence of excess isobutane and sulfuric acid catalyst to form a second reactor effluent comprising a second spent acid, a second alkylate, excess isobutane, normal butane, and propane;

e. a second acid decanter in fluid communication with the second reactor through a third conduit which conveys the second reactor effluent to the second acid decanter, which decanter separates the second reactor effluent into a second hydrocarbon phase and a second acid recycle phase;

f. a second deisobutanizer in fluid communication with the second acid decanter through a fourth conduit which conveys the second hydrocarbon phase to the second deisobutanizer, which deisobutanizer separates the second hydrocarbon phase into a second isobutane recycle stream and a second alkylate-rich intermediate product, the second deisobutanizer also producing a n-butane rich slip stream; and g. a common debutanizer in fluid communication with (1) the first deisobutanizer through a fifth conduit which conveys the first alkylate-rich intermediate product to the common debutanizer, and (2) the second deisobutanizer through a sixth conduit which conveys the n-butane rich slip stream from the second deisobutanizer to the common debutanizer, the common debutanizer separating the first alkylate-rich intermediate product and the n-butane rich slip stream into a n-butane and lighter hydrocarbon product and a first alkylate product.

7. An apparatus in accordance with claim 6 further comprising a seventh conduit which directs at least a portion of said first acid recycle phase from the first acid decanter to said second reactor.

8. An apparatus in accordance with claim 6 wherein the sixth conduit is adapted to direct at least a portion of the n-butane rich slip stream from the second deisobutanizer to the first deisobutanizer.

* * * * *